United States Patent
Hutchison et al.

(10) Patent No.: US 9,962,172 B2
(45) Date of Patent: May 8, 2018

(54) LIGAMENT BALANCER AND DRILL GUIDE

(71) Applicant: Biomet Manufacturing, LLC., Warsaw, IN (US)

(72) Inventors: Nicholas William Hutchison, Chippenham (GB); Russell Lloyd, Swindon (GB); David Wycliffe Murray, Oxford (GB); Christopher Dodd, Oxford (GB)

(73) Assignee: Biomet Manufacturing, LLC, Warsaw, IN (US)

( * ) Notice: Subject to any disclaimer, the term of this patent is extended or adjusted under 35 U.S.C. 154(b) by 443 days.

(21) Appl. No.: 14/854,795

(22) Filed: Sep. 15, 2015

(65) Prior Publication Data
US 2016/0074053 A1 Mar. 17, 2016

Related U.S. Application Data

(63) Continuation of application No. 13/206,787, filed on Aug. 10, 2011, now Pat. No. 9,168,032.

(30) Foreign Application Priority Data

Aug. 11, 2010 (GB) .................................. 1013470.8

(51) Int. Cl.
*A61B 17/16* (2006.01)
*A61B 17/17* (2006.01)
(Continued)

(52) U.S. Cl.
CPC ........ *A61B 17/1764* (2013.01); *A61B 17/025* (2013.01); *A61B 17/1675* (2013.01);
(Continued)

(58) Field of Classification Search
CPC ..... A61B 17/025; A61B 17/15; A61B 17/154; A61B 17/155; A61B 17/157;
(Continued)

(56) References Cited

U.S. PATENT DOCUMENTS 4,703,751 A  11/1987  Pohl
4,825,857 A *  5/1989  Kenna .................. A61B 17/154
                                                    606/88
(Continued)

FOREIGN PATENT DOCUMENTS

DE      4016704 C1    9/1991
EP      0720834 A2    7/1996
(Continued)

OTHER PUBLICATIONS

"U.S. Appl. No. 13/206,787, Examiner Interview Summary dated Apr. 10, 2013", 3 pgs.
(Continued)

*Primary Examiner* — Christian Sevilla
*Assistant Examiner* — Tracy Kamikawa
(74) *Attorney, Agent, or Firm* — Schwegman Lundberg & Woessner, P.A.

(57) ABSTRACT

A ligament balancer for a knee is disclosed that includes a first guide portion having a first guide hole extending there through, and a second guide portion having a second guide hole extending there through, the first and second guide portions being moveable with respect to each other along a movement axis, the balancer being adapted such that, in use, the movement axis is substantially parallel to the anterior/posterior axis of a distal femoral surface. Also disclosed is a kit of parts that includes the ligament balancer and a drill guide for a knee, the drill guide includes first and second connected arms, each arm comprising at least two guide openings extending there through, the guide openings being spaced longitudinally along each arm, longitudinal axes of the first and second arms intersecting at a predetermined angle. Also disclosed is a method of attaching a cutting block to a distal femoral surface as part of a knee replacement procedure.

18 Claims, 3 Drawing Sheets

(51) Int. Cl.
*A61B 17/72* (2006.01)
*A61B 17/02* (2006.01)
*A61B 17/15* (2006.01)
*A61B 19/00* (2006.01)
*A61F 2/46* (2006.01)
*A61B 90/00* (2016.01)

(52) U.S. Cl.
CPC ............ *A61B 17/72* (2013.01); *A61B 17/155* (2013.01); *A61B 2017/0268* (2013.01); *A61B 2019/545* (2013.01); *A61B 2090/061* (2016.02); *A61F 2002/4658* (2013.01)

(58) Field of Classification Search
CPC . A61B 17/1675; A61B 17/17; A61B 17/1714; A61B 17/1739; A61B 17/1764; A61B 17/1767; A61B 2017/0256; A61B 2017/0268; A61B 2017/0275; A61B 2019/461; A61B 2019/464
See application file for complete search history.

(56) References Cited

U.S. PATENT DOCUMENTS

| | | | |
|---|---|---|---|
| 5,141,513 | A | 8/1992 | Fortune et al. |
| 5,445,642 | A * | 8/1995 | McNulty .............. A61B 17/155 606/102 |
| 5,454,816 | A | 10/1995 | Ashby |
| 5,540,696 | A | 7/1996 | Booth, Jr. et al. |
| 5,634,927 | A | 6/1997 | Houston et al. |
| 5,649,929 | A | 7/1997 | Callaway |
| 5,688,280 | A | 11/1997 | Booth, Jr. et al. |
| 5,735,904 | A | 4/1998 | Pappas |
| 6,022,377 | A | 2/2000 | Nuelle et al. |
| 6,290,704 | B1 | 9/2001 | Burkinshaw et al. |
| 6,514,253 | B1 | 2/2003 | Yao |
| 9,168,032 | B2 | 10/2015 | Hutchison et al. |
| 2004/0167531 | A1 | 8/2004 | Hodorek |
| 2004/0230302 | A1 | 11/2004 | May et al. |
| 2007/0135924 | A1 | 6/2007 | Verhoogen |
| 2007/0239157 | A1* | 10/2007 | Guillaume ........... A61B 17/025 606/60 |
| 2008/0275451 | A1 | 11/2008 | Mcallister et al. |
| 2009/0088763 | A1* | 4/2009 | Aram .................. A61B 17/155 606/88 |
| 2009/0125114 | A1 | 5/2009 | May et al. |
| 2009/0222014 | A1 | 9/2009 | Bojarski et al. |
| 2012/0172881 | A1 | 7/2012 | Hutchison et al. |

FOREIGN PATENT DOCUMENTS

| | | |
|---|---|---|
| EP | 0903111 A2 | 3/1999 |
| EP | 0979636 A2 | 2/2000 |
| EP | 1643916 A2 | 4/2006 |
| FR | 2679766 A1 | 2/1993 |
| FR | 2857576 A1 | 1/2005 |
| FR | 2899091 A1 | 10/2007 |
| GB | 2215610 A | 9/1989 |
| GB | 2434747 A | 8/2007 |
| GB | 2445620 A | 7/2008 |
| GB | 2475491 A | 5/2011 |
| JP | 2001346800 A | 12/2001 |
| JP | 2007075517 A | 3/2007 |
| WO | WO-0185038 A1 | 11/2001 |
| WO | WO-2005006993 A2 | 1/2005 |
| WO | WO-2006010871 A1 | 2/2006 |
| WO | WO-2006135462 A2 | 12/2006 |

OTHER PUBLICATIONS

"U.S. Appl. No. 13/206,787, Final Office Action dated Jan. 29, 2015", 16 pgs.
"U.S. Appl. No. 13/206,787, Final Office Action dated Jul. 17, 2013", 34 pgs.
"U.S. Appl. No. 13/206,787, Non Final Office Action dated Jan. 3, 2013", 12 pgs.
"U.S. Appl. No. 13/206,787, Non Final Office Action dated Jul. 18, 2014", 26 pgs.
"U.S. Appl. No. 13/206,787, Notice of Allowance dated Jun. 15, 2015", 7 pgs.
"U.S. Appl. No. 13/206,787, Response filed Apr. 3, 2013 to Non Final Office Action dated Jan. 3, 2013", 17 pgs.
"U.S. Appl. No. 13/206,787, Response filed May 29, 2015 to Final Office Action dated Jan. 29, 2015", 17 pgs.
"U.S. Appl. No. 13/206,787, Response filed Oct. 13, 2014 to Non Final Office Action dated Jul. 18, 2014", 20 pgs.
"U.S. Appl. No. 13/206,787, Response filed Oct. 17, 2013 to Final Office Action dated Jul. 17, 2013", 19 pgs.
"U.S. Appl. No. 13/206,787, Response filed Dec. 5, 2012 to Restriction Requirement dated Nov. 21, 2012", 1 pg.
"U.S. Appl. No. 13/206,787, Restriction Requirement dated Nov. 21, 2012", 9 pgs.

* cited by examiner

LIGAMENT BALANCER AND DRILL GUIDE

CROSS-REFERENCE TO RELATED APPLICATIONS

This application is a continuation of U.S. patent application Ser. No. 13/206,787 filed Aug. 10, 2011, now issued as U.S. Pat. No. 9,168,032, which claims benefit of United Kingdom Patent Application No. 1013470.8 filed on Aug. 11, 2010, the benefit of priority of each of which is claimed hereby, and each of which are incorporated by reference herein in its entirety.

FIELD

The present invention relates to tools for use in knee surgery and particularly to a ligament balancer and a drill guide for a knee.

BACKGROUND

When a knee joint becomes damaged or diseased, it is known to replace all or part of the knee joint with a prosthesis. A common form of prosthesis comprises a femoral component, which is attached to a distal end of a femur, and a tibial component, which is attached to a proximal end of a tibia. The femoral and tibial components may articulate directly or may be separated by a meniscal bearing component. The femoral component also articulates with a patella, which is secured in position by a quadriceps tendon and a patellar ligament.

The articulation of a natural knee joint is stabilised by the action of medial and lateral collateral ligaments and anterior and posterior cruciate ligaments. Where possible, all of these ligaments are retained when a prosthesis is implanted, although in practice it is often necessary to remove at least the posterior cruciate ligament. It is desirable for tension in the knee ligaments after surgery to be balanced throughout the range of motion of the knee.

The most complex component of a knee prosthesis is the femoral component, as it carries not only the condylar bearing surfaces, but also the patella bearing surface, which extends along an anterior face of the distal femur. Conventional femoral components require resection of the distal end surface of the femur and the anterior and posterior faces of the femur. They also usually require two chamfered cuts to be made at the distal end of the femur anteriorly and posteriorly. The positioning of the femoral cuts determines the position and orientation of the implanted femoral component, and hence the bearing surfaces which it carries. The correct positioning of the femoral cuts is vitally important therefore to ensuring equal tension in the ligaments after surgery.

It is known to use surgical jigs to guide the positioning of the femoral cuts. Correct placing of a jig to ensure balancing of the ligaments with the knee in flexion is complicated by the presence of the patella. The patella is conventionally either everted or subluxed in order to provide sufficient space for the surgical jig. However, this means that the substantial force exerted via the patella and patellar tendon by the quadriceps mechanism is acting out of its normal alignment. With the patella out of position, this force acts to skew the joint either laterally or medially, making balancing of the remaining ligaments extremely difficult.

Owing, at least in part, to the complicated nature of balancing ligaments with the knee in flexion, flexion balancing conventionally comprises attempting to replicate in flexion a previously measured and balanced extension gap.

SUMMARY

According to a first aspect, there is provided a ligament balancer for a knee, comprising a first guide portion having a first guide hole extending there through, and a second guide portion having a second guide hole extending there through, the first and second guide portions being moveable with respect to each other along a movement axis, the balancer being adapted such that, in use, the movement axis is substantially parallel to the anterior/posterior axis of a distal femoral surface.

The first and second guide holes may be aligned along an axis that is substantially parallel to the movement axis of the balancer.

The ligament balancer may further comprise a tibial location plate which may be rigidly connected to the first guide portion. The tibial location plate may be integrally formed with the first guide portion. The tibial location plate may define a tibial location plane which may be substantially perpendicular to the movement axis of the ligament balancer.

The ligament balancer may further comprise at least one tibial spacer which may be removably connected to the tibial location plate.

The tibial spacer may be removably connected to the tibial location plate by cooperating attachment means formed on the tibial spacer and tibial location plate.

The cooperating attachment means may comprise a recessed groove and projecting rib. The recessed groove may be formed on the tibial location plate, with the corresponding projecting rib formed on the tibial spacer plate.

The tibial location plate attachment means may be located on a face of the tibial location plate that is remote from the second guide portion and remainder of the ligament balancer, so as to be adjacent to a tibia when the balancer is in use.

The ligament balancer may further comprise a plurality of tibial spacer plates, each one of which may be operable for removable connection to the tibial location plate, and each one of which may have a different thickness.

The ligament balancer may further comprise an intramedullary rod which may be rigidly connected to the second guide portion. The intramedullary rod may be integrally formed with the second guide portion.

The second guide hole extending through the second guide portion may be spaced away from the intramedullary rod in a direction that is substantially perpendicular to the movement axis of the balancer.

The axis of alignment of the first and second guide holes may be spaced away from the intramedullary rod in a direction that is substantially perpendicular to the axis of alignment of the first and second guide holes.

The ligament balancer may further comprise a drive mechanism operating between the first and second guide portions. The drive mechanism may be a pinion drive.

At least one of the first and second guide portions may comprise a post that extends substantially parallel to the movement axis of the balancer and carries a rack, the post being received within an opening which may be formed on the other of the first and second guide portions.

According to a second aspect, there is provided a ligament balancer for a knee comprising a tibial location plate that defines a plane, an intramedullary rod extending substantially parallel to the plane of, and moveably connected to the tibial location plate, and at least one tibial spacer, adapted to be removably connected to the tibial location plate.

The tibial location plate may be adapted to receive the at least one tibial spacer on a surface of the plate that is remote from the intramedullary rod.

The tibial location plate may comprise a guide portion extending from the plane of the plate towards the intramedullary rod and having a guide hole extending there through.

The intramedullary rod may comprise a guide portion extending from a base of the rod and having a guide hole extending there through. The guide portion may extend towards the tibial location plate.

The ligament balancer may further comprise a drive mechanism operating between the tibial location plate and the intramedullary rod.

According to a third aspect, there is provided a drill guide for a knee, comprising first and second connected arms, each arm comprising at least two guide openings extending there through, the guide openings being spaced longitudinally along each arm, longitudinal axes of the first and second arms intersecting at a predetermined angle.

The at least two guide openings on each of the first and second arms may be located along the longitudinal axes of the respective arms.

At least one of the openings may comprise a slot extending along a longitudinal axis of an arm.

At least one of the openings may comprise a hole centred on a longitudinal axis of an arm.

The longitudinal axes of the first and second arms may intersect at 90 degrees.

The guide openings on one of the first and second arms may comprise at least a hole and a slot and the guide openings on the other of the first and second arms may comprise at least two holes.

The first and second arms may be connected in a T shape.

The first and second arms together may define a drill guide plane, and the guide openings may extend through the first and second arms along axes that are substantially non parallel to the drill guide plane.

The guide openings may extend through the first and second arms along axes that are substantially perpendicular to the drill guide plane.

A guide opening on the first arm may be coincident with a guide opening on the second arm.

One of the arms may comprise a reference arm and the other of the arms may comprise a drilling arm.

The guide openings on the reference arm may comprise at least a hole and a slot and the guide openings on the drilling arm may comprise at least two holes.

The guide holes on the drilling arm may define a drilling direction that is substantially perpendicular to a drill guide plane defined by the drilling and reference arms.

According to another aspect, there is provided a surgical kit of parts comprising a ligament balancer of the first and/or second aspects and a drill guide of the third aspect.

According to another aspect, there is provided a method of locating a cutting block on a distal femoral surface as part of a knee replacement procedure, comprising determining the anterior/posterior location of the cutting block solely from a measured extension gap of the knee.

The method may comprise: measuring the extension gap of the knee, selecting a guiding instrument corresponding to the measured extension gap, and using the guiding instrument to mark a location for the cutting block in the anterior/posterior direction. The guiding instrument may guide a marking tool in marking the location.

The guiding instrument may comprise a standard part and a changeable part, and selecting the guiding instrument may comprise selecting the changeable part that corresponds to the measured extension gap. The guiding instrument may comprise a ligament balancer according to the first and/or second aspects and the changeable part may comprise a tibial spacer plate.

Marking a location for the cutting block may comprise drilling a marking hole. Alternatively, marking a location may comprise drilling a mounting hole for the cutting block.

According to another aspect, there is provided a method of balancing knee ligaments comprising: placing the knee joint in flexion, inserting an intramedullary rod into the medullary canal of the femur; and moving the intramedullary rod away from the tibia until the femur begins to rotate about the intramedullary rod.

The intramedullary rod may form part of a ligament balancer according to the first and/or second aspects.

According to another aspect, there is provided a method of locating a cutting block on a distal femoral surface as part of a knee replacement procedure, comprising balancing the knee ligaments, drilling marker holes into the distal femoral surface, referencing the marker holes to position a drill guide, drilling mounting holes through the drill guide, and mounting the cutting block on the distal femoral surface via the mounting holes.

Balancing the knee ligaments may comprise placing the knee joint in flexion, inserting an intramedullary rod into the medullary canal of the femur; and moving the intramedullary rod away from the tibia until the femur begins to rotate about the intramedullary rod. The patella may be placed in its anatomical position before the joint is distracted by moving the intramedullary rod away from the tibia.

Balancing the knee ligaments may be conducted using a ligament balancing instrument. The marker holes may be drilled through the ligament balancing instrument. The ligament balancing instrument may be a ligament balancer according to the first and/or second aspects. The ligaments may be allowed to become out of balance once the marker holes have been drilled. The drill guide may be a drill guide according to the third aspect.

Referencing the marker holes to position a drill guide may comprise inserting pins into the marker holes and mounting the drill guide on the pins.

The marker holes may be aligned along a marking axis that intercepts a mounting axis along which the mounting holes are aligned. The marking axis may intersect the mounting axis at substantially 90 degrees. Each mounting hole may be displaced from the marking axis in substantially the same direction.

According to another aspect, there is provided a method of attaching a cutting block to a distal femoral surface as part of a knee replacement procedure, the method comprising:

a.) performing distal femoral and proximal tibial resections;

b.) measuring the resulting joint gap with the knee in extension;

c.) placing the knee in 90 degrees of flexion;

d.) inserting an intramedullary rod of a surgical instrument into the medullary canal of the femur;

e.) moving the intramedullary rod of the surgical instrument away from the proximal tibial surface until the femur begins to rotate about the intramedullary rod;

f.) drilling mounting holes for the cutting block into the distal femoral surface; and g.) mounting the cutting block via the drilled mounting holes.

The surgical instrument may comprise a ligament balancer according to the first and/or second aspects.

Part (c) may comprise adjusting soft tissues to balance the joint and/or achieve a rectangular joint gap. Part (c) may also comprise selecting an appropriate tibial spacer plate for the ligament balancer based upon the measured extension gap.

Part (f) may comprise drilling through guide holes on the surgical instrument.

Part (f) may comprise:
(i): drilling marker holes through the ligament balancer;
(ii) removing the ligament balancer and mounting a drill guide via the marker holes; and
(iii) drilling mounting holes through the drill guide.

At least part of Part (f) may be conducted while the femur is in the position attained at the end of Part (e).

Part (f)(i) may be conducted with the patella in its anatomical position.

The drill guide may comprise a drill guide according to the third aspect.

Part (e) may be conducted with the patella in its anatomical position.

BRIEF DESCRIPTION OF THE DRAWINGS

For a better understanding of the present invention, and to show more clearly how it may be carried into effect, reference will now be made, by way of example, to the following drawings, in which.

DETAILED DESCRIPTION OF THE DRAWINGS

The ligament balancer and drill guide are suitable for use in a knee replacement procedure. An extension gauge and knee sizer may also be used as part of the same knee replacement procedure.

Figure 1:
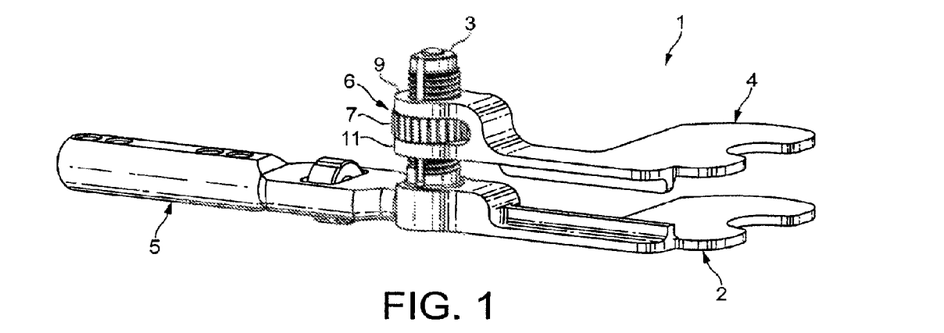
FIG. 1 is a perspective view of an extension gauge for a knee.

With reference to FIG. 1, an extension gauge 1 comprises a tibial location plate 2, a substantially parallel femoral location plate 4, a handle 5, a drive mechanism 6, that moves the tibial and femoral location plates relative to each other, and a referencing scale (not shown). The drive mechanism comprises a threaded post 3 extending from the tibial location plate 2, in a direction substantially perpendicular to the plane of the plate 2, and a cooperating nut that is received on the threaded post 3 and contained between bifurcated arms 9, 11 extending from the femoral location plate 4. Rotation of the nut 7 causes translation of the nut 7 and femoral location plate 4 along the threaded post 3.

In use, the extension gauge 1 is employed following resection of the distal femoral and proximal tibial surfaces. The gauge 1 is inserted into the knee joint space via the handle 5 with the knee in extension. The tibial and femoral location plates 2, 4 are then separated using the drive mechanism 6 until each plate 2, 4 rests against the corresponding resected surface of the tibia or the femur. The collateral ligaments may then be adjusted so that the extension gap between the resected surfaces is rectangular, the planar faces of the location plates 2, 4 fully engaging the resected bone surfaces of the tibia and femur. The size of the balanced extension gap may then be read from the scale on the extension gauge.

Figure 2:
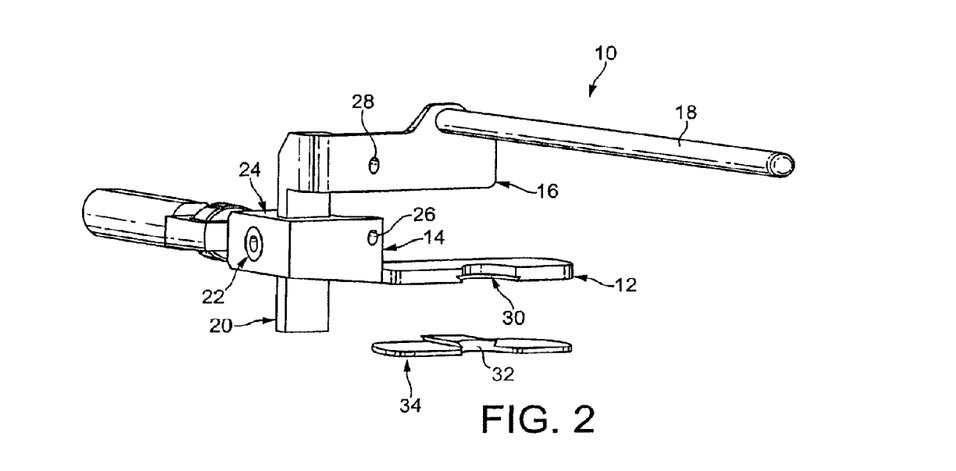
FIGS. 2 and 3 are perspective views of a ligament balancer for a knee.
Figure 3:
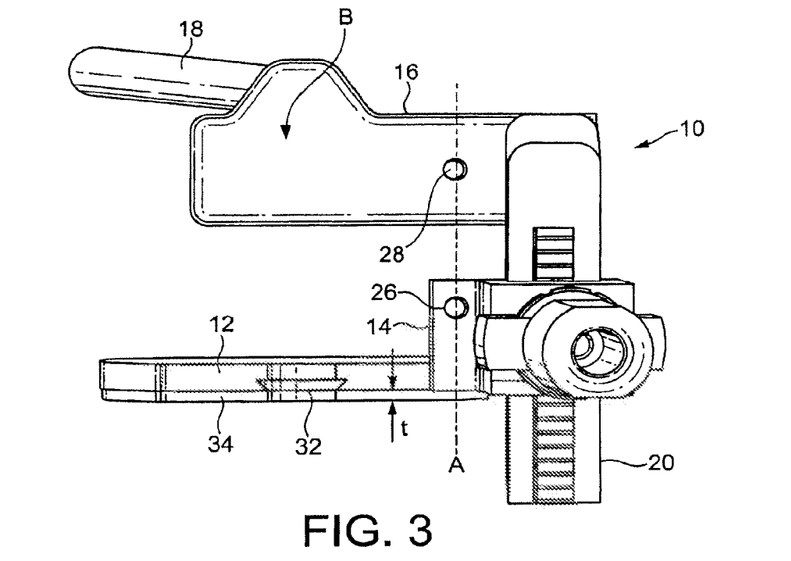

With reference to FIGS. 2 and 3, a ligament balancer 10 comprises a tibial location plate 12, a first guide portion 14 integrally formed with the tibial location plate 12, a second guide portion 16 and an intramedullary (IM) rod 18 integrally formed with the second guide portion 16. The first and second guide portions 14, 16 extend in a plane that is substantially perpendicular to the plane of the tibial location plate 12 and the plane in which the axis of the IM rod 18 extends. The second guide portion 16 is also integrally formed with a mounting post 20 which extends away from the second guide portion 16 to be received in an opening 24 on the first guide portion. A hex pinion drive 22 acts between the mounting post 20 of the second guide portion 16 and the first guide portion 14 to enable controlled separation of the tibial location plate 12/first guide portion 14 and the IM rod 18/second guide portion 16. Guide holes 26, 28 extend through the first and second guide portions 14, 16 respectively, so that the guide holes 26, 28 may be separated as the first and second guide portions 14, 16 are separated using the hex pinion drive 22. The guide holes 26, 28 are aligned along an axis A that is perpendicular to the plane of the tibial location plate 12. As illustrated particularly in FIG. 3, the guide holes 26, 28 are displaced away from the axis of the IM rod 18 such that the axis A along which the guide holes 26, 28 are aligned is displaced from the IM rod in a direction that is perpendicular to the axis of alignment A of the guide holes. A lower (as viewed in the figures) surface of the tibial location plate 12 comprises a groove 30, operable to receive a cooperating protruding rib 32 on a tibial spacer plate 34. The lower surface of the tibial location plate 12 is that surface which is distant from the IM rod 18 and the remainder of the balancer 10. A plurality of tibial spacer plates 34 is provided, each having a different thickness t. Further detail of the ligament balancer 10 is provided in the discussion of an operative technique below.

Figure 4:
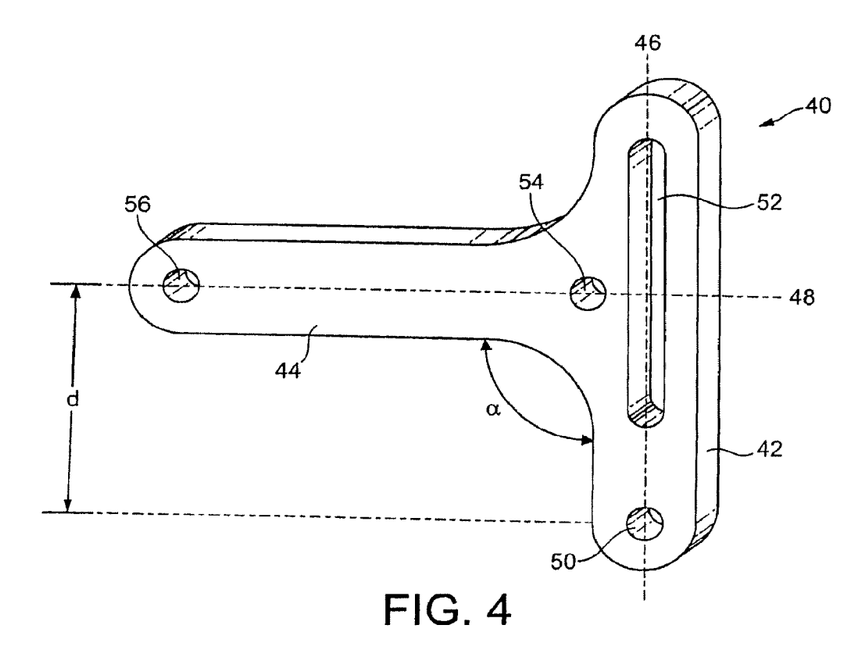
FIG. 4 is a perspective view of a drill guide.

With reference to FIG. 4, a drill guide 40 comprises a first, or reference, arm 42 and a second, or drilling, arm 44 that is rigidly connected to the reference arm 42. The arms 42, 44 are connected at a fixed angle α of 90 degrees so as to form a T shape that defines a guide plane of the tool 40. Guide openings extend through each of the arms 42, 44 along the longitudinal reference axis 46 of the reference arm 42 and the longitudinal drilling axis 48 of the drilling arm 44. The reference arm 42 comprises a first guide opening in the form of a reference hole 50 and a second guide opening in the form of a reference slot 52. The drilling arm 44 comprises two guide openings in the form of drill holes 54, 56. Each of the guide openings extends through the drill guide in a direction perpendicular to the plane of the drill guide. The reference slot 52 additionally extends longitudinally within the plane of the drill guide along the reference axis 46. The drill guide 40 acts as a translation guide, enabling holes to be drilled through the guide openings 54, 56 on the drilling arm 44 in a fixed special relation to existing input holes, registered by the reference arm 42 through the interaction of pins inserted into the input holes and extending into the reference hole 50 and reference slot 52. The reference slot 52 on the reference arm 42 allows for varying separation in the input holes to be accommodated.

In use, pins are inserted into the above mentioned input holes and the drill guide 40 is mounted on the pins via the reference hole 50 and reference slot 52 in the reference arm 42. Holes can then be drilled through the drill guide holes 54, 56 in the drilling arm, with the drilling direction being at 90 degrees to the plane of the drill guide. The newly drilled holes are aligned on an axis that is at 90 degrees to the axis aligning the input holes, which corresponds to the reference axis 46 of the drill guide 40, when the drill guide is mounted on the input holes via the pins. The vertical (as viewed in FIG. 4) location of the newly drilled holes is determined by the vertical (as viewed in FIG. 4) location of the lower of the input holes, that which corresponds to guide hole 50 on the reference arm 42.

Figure 5:
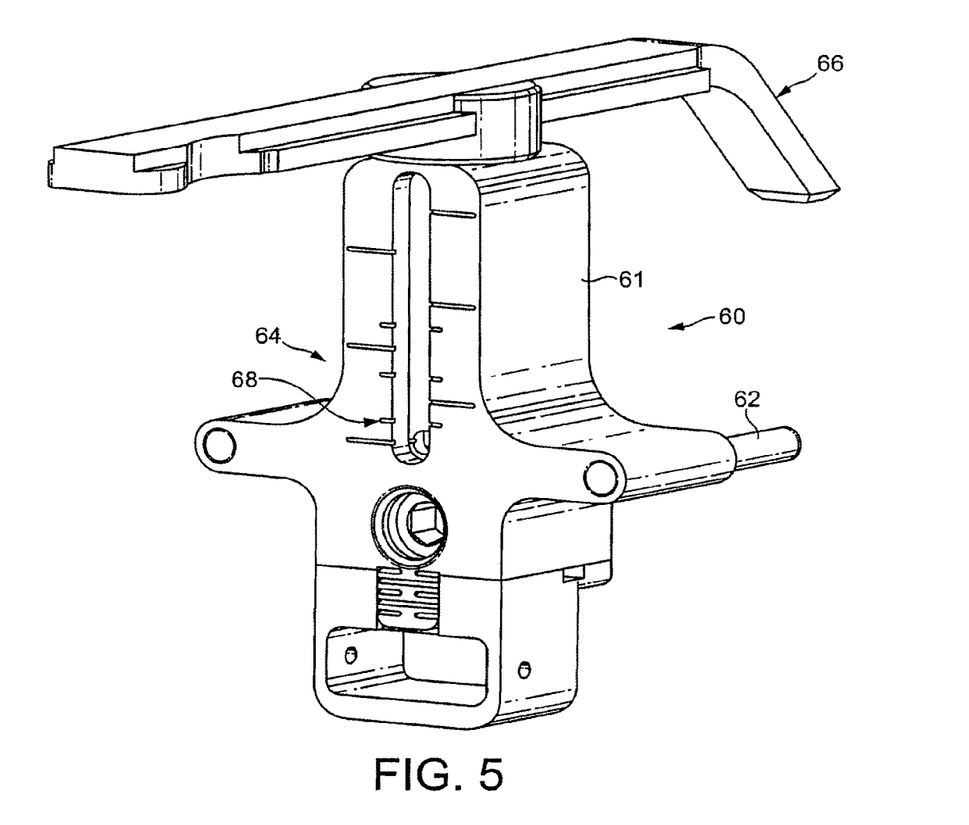
FIG. 5 is a perspective view of a knee sizer.

With reference to FIG. 5, an Anterior/Posterior (A/P) sizer 60 comprises a body 61, mounting posts 62, 64 extending from the body 61, a stylus 66 mounted on the body 61 and reference means 68 marked on the body 61. In use, the A/P sizer 60 is mounted in appropriate holes in a distal femoral surface via the mounting posts 62, 64 and the stylus 66 is used, in combination with the reference means 68, to measure the size of the anterior portion of a femur.

An operative technique for total knee replacement that employs the above described instruments is as follows:

The distal femoral and proximal tibial cuts are made to the femur and tibia respectively in a conventional manner.

The leg is placed in extension and the extension gap is measured using the extension gauge 1. The collateral ligaments are adjusted to ensure that the gap is rectangular with equal tension in the ligaments.

The knee is placed in 90 degrees of flexion.

The measured extension gap is used to determine the requirement for and correct size of tibial spacer 34 to be attached to the tibial location plate 12 of the ligament balancer 10. Table 1 demonstrates how the measured extension gap is correlated to the required tibial spacer.

TABLE 1

| Measured Extension Gap | Tibial Spacer Plate Required |
|---|---|
| 10 mm | No spacer required |
| 12 mm | Size 12 spacer required |
| 14 mm | Size 14 spacer required |
| 16 mm | Size 16 spacer required |
| 18 mm | Size 18 spacer required |

The patella is everted or subluxed, the medullary canal of the femur is opened and the IM rod 18 of the ligament balancer 10 is inserted into the medullary canal until the second guide portion 16 is flush with the resected distal femoral surface.

The patella is returned to its anatomical position, resting over the second guide portion 16 in the region of area B on FIG. 3.

The ligament balancer 10 is opened using the hex pinion drive 22, separating the tibial location plate 12/first guide portion 14 and the IM rod 18/second guide portion 16 until ligament slack is taken up. The extent to which ligament slack has been taken up can be assessed by observation of the femur. At the point at which ligament slack is completely taken up, the femur begins to rotate about its longitudinal axis and hence about the IM rod 18. The ligament balancer 10 is therefore opened until the femur begins to rotate on the IM rod 18. It will be appreciated that the flexion gap is not measured, neither is it forced to assume a predetermined magnitude, the balancer 10 is simply opened until the slack is taken up. Use of the tibial spacer plates 34 ensures that the ligament balancer 10 is not required to open a great distance, even with a relatively large joint space, meaning the ligament balancer 10 can remain relatively small and compact.

With ligament slack taken up, at the point where the femur is just beginning to rotate on the IM rod 18, pin holes are drilled through the guide holes 26, 28 in the first and second guide portions 14, 16 of the balancer 10 into the resected femoral surface. It will be appreciated that the anterior/posterior location of the lower guide hole 26, and hence the drilled lower pin hole, is determined by the presence and size of tibial spacer 34, and hence by the measured extension gap, in combination with the fixed geometry of the balancer 10. It will also be appreciated that the anterior/posterior separation of the guide holes 26, 28 is not important; the important feature is that the drilled pin holes guided by them are in "vertical" anterior/posterior alignment on the femur at the point at which the ligaments are correctly tensioned, that is the point at which the femur just begins to rotate about the IM rod 18. The lateral separation of the guide holes 26, 28 away from the IM rod 18 ensures that the pin holes can be drilled with the patella in place, and thus with the forces of the joint acting in their anatomical directions. The guide holes 26, 28 are a suitable distance away from the patella, when it is in place over the region B of the ligament balancer 10, that the pin holes may be safely drilled through the guide holes 26, 28 without risking damage to the patella or surrounding soft tissues.

The patella is again everted or subluxed and the ligament balancer 10 is removed from the joint space.

Pins are inserted into the two drilled pin holes in the resected femoral surface and the drill guide 40 is mounted onto the pins via the reference hole 50 and the reference slot 52 in the reference arm 42.

Mounting peg holes are drilled through the two unoccupied drill guide holes 54, 56 on the drilling arm 44 of the drill guide 40. The drill guide 40 ensures that the two new peg holes are orthogonal to the vertical (as seen in FIG. 4) anterior/posterior axis defined by the two pin holes drilled using the ligament balancer 10. The newly drilled peg holes are thus aligned with the horizontal (as seen in FIG. 4) medial/lateral axis when the knee is correctly balanced. The vertical (as seen in the Figures) anterior/posterior location of the newly drilled peg holes is determined by the anterior/posterior location of the lower ligament balancer guide hole 26, hence by the measured extension gap, in combination with the fixed geometry of the drill guide 40. The combined effect of the ligament balancer 10 and drill guide 40 is that the position of the eventual horizontally aligned (as seen in the Figures) mounting peg holes is determined with the patella in place. The horizontally aligned peg holes cannot be directly drilled with the patella in place because the patella is in the way, but by using the drill guide 40 and the vertically aligned pin holes that are drilled using the ligament balancer 10 with the patella in place, the eventual location of the horizontally aligned peg holes is fixed while the patella is in place and the knee is accurately balanced.

The drill guide 40 and pins are removed and the A/P sizer 60 is mounted via the mounting posts 62, 64 on the horizontally aligned mounting peg holes drilled through the drill guide 40. The stylus 66 references off the anterior portion of the femur to size the femur and thus establish what size of cutting block should be employed to make the remaining anterior, posterior and chamfered cuts to the femur.

The A/P sizer 60 is removed and the appropriate size cutting block is mounted in the same horizontally aligned mounting peg holes. It is envisaged that all cutting blocks to be used with this technique would have the same separation between the mounting pegs and the posterior cut guide surface. It is only the separation between the mounting pegs and the anterior cut guide surface that would vary, and it is this separation that is established by the A/P sizer 60.

Anterior, posterior and chamfered cuts are made and the operation is continued in a conventional manner.

As discussed above, the anterior, posterior and chamfered cuts made to the distal femur determine the final position of the femoral component, and their correct positioning is therefore of fundamental importance to ensuring post operative performance of the prosthetic joint. The position of these cuts is determined by the location at which a cutting block is mounted on the resected surface of the distal femur. Cutting blocks are conventionally mounted via two mounting peg holes which are aligned substantially in the medial/lateral direction on the resected distal femoral surface with the knee in 90 degrees of flexion. Determining the appropriate position for these peg holes is extremely challenging, as their correct position can only truly be determined with all the ligaments that exert forces on the joint in their correct anatomical positions, and yet the mounting peg holes will in inevitably need to be located in very close proximity to an anatomically located patella.

The majority of existing surgical instrumentation designed to assist in locating mounting holes for a femoral cutting block inherently accepts that ligament balancing and drilling of the peg holes cannot be performed with the patella in its anatomical position. Those few instruments that do seek to work with the patella in place look to reduce the size of the instrument, such that it can be accommodated behind the patella. However, the basic functioning of these instruments is conventional.

The present system represents a fundamental departure from the conventional approach to locating the mounting peg holes for a femoral cutting block. The present system separates the actions of balancing the knee ligaments and drilling the cutting block mounting holes, such that the conditions for each action may be optimised. Thus, with the patella in place, the ligament balancer 10 allows the knee ligaments to be accurately balanced. Rather than forcing a flexion gap to match an extension gap, the ligament balancer 10 allows a surgeon to recognise when the soft tissues of the knee are in balance, by visually registering the moment at which the femur begins to rotate about its longitudinal axis. Instead of trying to drill the cutting block mounting holes at this time, the ligament balancer 10 instead guides the drilling of two marker holes, that are in correct anterior/posterior alignment when the knee joint is balanced in 90 degrees of flexion. As these holes merely serve a marking or indicating function, they can be located away from the line of action of the patella and thus can be drilled with the patella in place and without risking damage to the patella and its supporting soft tissues. Once the marker holes have been drilled, the final position of the cutting block has effectively been established, and there is no longer any need to maintain the knee ligaments in their balanced condition. The patella can be everted or subluxed and the ligament balancer 10 removed to reveal the resected distal femoral surface with its two marker holes.

The relation between the marker holes, drilled with the knee in balance, and the final location of the cutting block mounting holes is fixed by the features of the drill guide 40. This drill guide 40 in effect operates as a translation guide or template, with input reference features and output drilling features in a fixed spatial arrangement. Via the drill guide 40 of the present system, the more posterior of the marker holes fixes the anterior/posterior location of the cutting block mounting holes, and the alignment of the two marker holes in the anterior/posterior direction fixes the alignment of the cutting block mounting holes in the medial/lateral direction.

The drill guide 40 comprises two drilling holes 54, 56, through which the cutting block mounting holes are drilled, that are a fixed distance d from the posterior reference hole 50 in the anterior/posterior direction (when the drill guide is in position on a distal femoral surface). The cutting block mounting holes are thus drilled at an anterior/posterior level that is the fixed distance d above the posterior marking hole. The anterior marking hole provides an alignment axis that marks the precise anterior posterior axis at which the knee is balanced. The reference slot 52 in the drill guide 40 accommodates considerable variation in location of the anterior marker hole, as it is the axis that this hole defines in combination with the posterior marker hole, rather than the precise location of the anterior marker hole, which is important.

In order for the correct femoral cuts to be made, the cutting block mounting holes should be aligned along the precise medial/lateral axis at which the knee ligaments are balanced. When the posterior reference hole 50 of the drill guide 40 is aligned with the posterior marker hole (via a pin) and the reference slot 52 of the drill guide 40 is aligned with the anterior marker hole (also via a pin), the reference axis 46 of the drill guide 40 is in alignment with the balanced anterior/posterior axis defined by the marker holes. The drilling axis 48 of the drill guide 40, on which the drilling holes 54, 56 of the guide 40 are located, is thus oriented at 90 degrees to this balanced anterior/posterior axis. In this manner, no matter what the actual orientation of the femur might be at the time of drilling, the cutting block mounting holes drilled through the drill holes 54, 56 of the drill guide 40 will be aligned along the precise medial/lateral axis at which the knee is balanced. It will be appreciated that the drilling of the cutting block mounting holes can therefore be conducted without concern for the balancing of the knee ligaments at the time of drilling, and with the patella safely out of the way. It will further be appreciated that this separation of the ligament balancing and mounting hole drilling operations optimises conditions for both operations, and represents a significant departure from the operation of known instrumentation for guiding the drilling of such holes.

The use of tibial spacer plates 32 in the ligament balancer 10 of the present system enables the ligament balancer 10 to be optimised to the particular joint space in which it must work. In a large joint space, having a large extension gap, a thick tibial spacer plate can be employed, raising the tibial location plate 12 and hence also the guide hole 26 through which the posterior marking hole is drilled. The anterior/posterior location of this hole, and hence of the cutting block mounting holes, is thus matched to the available joint space. In addition, by raising the tibial location plate 12 relative to the femur, the distance by which the tibial location plate 12 and IM rod 18 must be separated is reduced, enabling the ligament balancer 10 to remain compact for working in smaller joint spaces and with the patella in its anatomical position.

It will be appreciated that, while specific embodiments of the present system have been described, these embodiments are not intended to limit the scope of the present system. Thus, variations to the described embodiments may be contemplated. For example the geometric arrangement of the drill guide 40 may be varied, in order to provide the desired translation relation between input marker holes and drilled mounting holes. In addition, and to the extent physically possible, features described in relation to any one embodiment may be employed in connection with any other embodiment described herein.

Statements Setting Out Additional Aspects

Statement 1: A ligament balancer for a knee, comprising a first guide portion having a first guide hole extending there through, and a second guide portion having a second guide hole extending there through, the first and second guide portions being moveable with respect to each other along a movement axis, the balancer being adapted such that, in use, the movement axis is substantially parallel to the anterior/posterior axis of a distal femoral surface.

Statement 2: The ligament balancer of statement 1, wherein the first and second guide holes are aligned along an axis that is substantially parallel to the movement axis of the balancer.

Statement 3: The ligament balancer of statement 1 or 2, further comprising a tibial location plate rigidly connected to the first guide portion.

Statement 4: The ligament balancer of statement 3, further comprising at least one tibial spacer, removably connected to the tibial location plate.

Statement 5: The ligament balancer of statement 4, wherein the tibial spacer is removably connected to the tibial location plate by cooperating attachment means on the tibial spacer and tibial location plate.

Statement 6: The ligament balancer of statement 5, wherein the cooperating attachment means comprise a recessed groove and projecting rib.

Statement 7: The ligament balancer of statement 6, wherein the tibial location plate attachment means is located on a face of the tibial location plate that is remote from the second guide portion and remainder of the ligament balancer.

Statement 8: The ligament balancer of any of statements 4 to 7, further comprising a plurality of tibial spacer plates, each one operable for removable connection to the tibial location plate, each tibial spacer plate having a different thickness.

Statement 9: The ligament balancer of any of the preceding statements, further comprising an intramedullary rod rigidly connected to the second guide portion.

Statement 10: The ligament balancer of statement 9 wherein the second guide hole extending through the second guide portion is spaced away from the intramedullary rod in a direction that is substantially perpendicular to the movement axis of the balancer.

Statement 11: The ligament balancer of statement 9, when dependent on statement 2, wherein the axis of alignment of the first and second guide holes is spaced away from the intramedullary rod in a direction substantially perpendicular to the axis of alignment of the first and second guide holes.

Statement 12: The ligament balancer of any of the preceding statements, further comprising a drive mechanism operating between the first and second guide portions.

Statement 13: The ligament balancer of statement 12, wherein at least one of the first and second guide portions comprises a post that extends substantially parallel to the movement axis of the balancer and carries a rack, the post being received within an opening formed on the other of the first and second guide portions.

Statement 14: A ligament balancer for a knee comprising a tibial location plate that defines a plane, an intramedullary rod extending substantially parallel to the plane of, and moveably connected to the tibial location plate, and at least one tibial spacer, adapted to be removably connected to the tibial location plate.

Statement 15: The ligament balancer of statement 14, wherein the tibial location plate is adapted to receive the at least one tibial spacer on a surface of the plate that is remote from the intramedullary rod.

Statement 16: The ligament balancer of statement 14 or 15, wherein the tibial location plate comprises a guide portion extending from the plane of the plate towards the intramedullary rod and having a guide hole extending there through.

Statement 17: The ligament balancer of any of statements 14 to 16, wherein the intramedullary rod comprises a guide portion extending from a base of the rod and having a guide hole extending there through.

Statement 18: The ligament balancer of any of statements 14 to 17, further comprising a drive mechanism operating between the tibial location plate and the intramedullary rod.

Statement 19: A drill guide for a knee, comprising first and second connected arms, each arm comprising at least two guide openings extending there through, the guide openings being spaced longitudinally along each arm, longitudinal axes of the first and second arms intersecting at a predetermined angle.

Statement 20: The drill guide of statement 19, wherein the at least two guide openings on each of the first and second arms are located along the longitudinal axes of the respective arms.

Statement 21: The drill guide of statement 19 or 20, wherein at least one of the openings comprises a slot extending along a longitudinal axis of an arm.

Statement 22: The drill guide of any of statements 19 to 21, wherein at least one of the openings comprises a hole centred on a longitudinal axis of an arm.

Statement 23: The drill guide of any of statements 19 to 22, wherein the longitudinal axes of the first and second arms intersect at 90 degrees.

Statement 24: The drill guide of any of statements 19 to 23, wherein the guide openings on one of the first and second arms comprise at least a hole and a slot and the guide openings on the other of the first and second arms comprise at least two holes.

Statement 25: The drill guide of any of statements 19 to 24, wherein the first and second arms are connected in a T shape.

Statement 26: The drill guide of any of statements 19 to 25, wherein the first and second arms together define a drill guide plane, and the guide openings extend through the first and second arms along axes that are substantially non parallel to the drill guide plane.

Statement 27: The drill guide of statement 26, wherein the guide openings extend through the first and second arms along axes that are substantially perpendicular to the drill guide plane.

Statement 28: The drill guide of any of statements 19 to 27, wherein a guide opening on the first arm is coincident with a guide opening on the second arm.

Statement 29: The drill guide of any of statements 19 to 28, wherein one of the arms comprises a reference arm and the other of the arms comprises a drilling arm.

Statement 30: The drill guide of statement 29, wherein the guide openings on the reference arm comprise a hole and a slot and the guide openings on the drilling arm comprise holes.

Statement 31: The drill guide of statement 30, wherein the guide holes on the drilling arm define a drilling direction that is substantially perpendicular to a drill guide plane defined by the drilling and reference arms.

Statement 32: A surgical kit of parts comprising the ligament balancer of any of statements 1 to 18 and the drill guide of any of statements 19 to 31.

What is claimed is:

1. A method of locating and mounting a cutting block on a distal femoral surface as part of a knee replacement procedure, comprising:

balancing knee ligaments of a knee joint;
drilling marker holes through a ligament balancer into the distal femoral surface;
referencing the marker holes to position a drill guide by removing the ligament balancer and mounting the drill guide via the marker holes;
drilling mounting holes through the drill guide; and
mounting the cutting block on the distal femoral surface via the mounting holes.

2. The method as claimed in claim 1, wherein balancing the knee ligaments comprises:
placing the knee joint in flexion;
inserting an intramedullary rod into a medullary canal of a femur; and
moving the intramedullary rod away from a tibia until the femur begins to rotate about the intramedullary rod.

3. The method as claimed in claim 2, wherein a patella is placed in its anatomical position before the knee joint is distracted by moving the intramedullary rod away from the tibia.

4. The method as claimed in claim 2, wherein placing the knee joint in flexion comprises one of adjusting soft tissues to balance the joint or achieve a rectangular joint gap and selecting an appropriate tibial spacer plate for the ligament balancer based upon a measured extension gap.

5. The method as claimed in claim 2, wherein at least part of drilling the mounting holes through the drill guide is conducted while the femur is in the position attained at the end of moving the intramedullary rod away from the tibia until the femur begins to rotate about the intramedullary rod.

6. The method as claimed in claim 2, wherein moving the intramedullary rod away from the tibia until the femur begins to rotate about the intramedullary rod is conducted with a patella in its anatomical position.

7. The method as claimed in claim 1, wherein drilling the marker holes through the ligament balancer is conducted with a patella in its anatomical position.

8. The method as claimed in claim 1, further comprising:
performing distal femoral and proximal tibial resections; and
measuring a resulting joint gap with the knee joint in extension before balancing the knee ligaments.

9. The method as claimed in claim 1, wherein the knee ligaments are balanced using the ligament balancer which comprises:
a first guide portion defining a first guide hole extending therethrough;
a second guide portion defining a second guide hole extending therethrough, the first and second guide portions being moveable with respect to each other along a movement axis of the ligament balancer, the first and second guide holes being aligned along an alignment axis that is substantially parallel to the movement axis of the balancer;
a mounting post extending between the first guide portion and the second guide portion along the movement axis and coupling the first and the second guide portions together; and
an intramedullary rod extending from the second guide portion, the intramedullary rod and the mounting post are on opposite sides of the alignment axis;
wherein the ligament balancer is adapted such that, in use, the movement axis is substantially parallel to an anterior/posterior axis of the distal femoral surface; and
wherein the first and second guide holes extend in parallel, spaced apart planes.

10. A method of locating and mounting a cutting block during a total knee replacement comprising:
making distal femoral and proximal tibial cuts to a femur and a tibia of a leg;
positioning a ligament balancer having first and second guide portions against a resected femoral surface, the first and second guide portions being movable relative to each other along a movement axis;
adjusting a position of the first and second guide portions along the movement axis to take up ligament slack;
drilling a pin hole through a guide hole in each of the first and second guide portions into the resected femoral surface;
inserting pins into the two drilled pin holes in the resected femoral surface;
mounting a drill guide onto the pins via a reference hole and a reference slot in a reference arm of the drill guide;
drilling mounting peg holes through two drill guide holes on a drilling arm of the drill guide to ensure that the two mounting peg holes are aligned orthogonally to the movement axis;
removing the drill guide and the pins;
mounting an A/P sizer on mounting posts inserted into the mounting peg holes;
selecting a cutting block size based on a measurement from the A/P sizer; and
making anterior, posterior and chamfered cuts to the femur using the selected cutting block.

11. The method of claim 10, further comprising measuring an extension gap with the leg in extension after making the distal femoral and proximal tibial cuts using an extension gauge.

12. The method of claim 11, further comprising selecting a thickness of a tibial spacer plate for the first guide portion of the ligament balancer based upon the measured extension gap.

13. The method of claim 12, wherein a distance between the guide holes in taking up the ligament slack is determined based on the thickness of the tibial spacer.

14. The method of claim 12, wherein positioning the ligament balancer further comprises:
placing a knee joint of the leg in flexion;
inserting an intramedullary rod extending from the second guide portion of the ligament balancer into a medullary canal of the femur; and
moving the intramedullary rod away from the tibia until the femur begins to rotate about the intramedullary rod.

15. The method of claim 10, wherein:
the movement axis is substantially parallel to an anterior/posterior axis of a distal femoral surface; and
the guide holes extend along parallel, spaced apart axes perpendicular to the movement axis.

16. The method of claim 15, wherein:
the guide holes are aligned along an alignment axis substantially parallel to the movement axis.

17. The method of claim 10, wherein selecting the cutting block size comprises referencing a stylus on the A/P sizer off an anterior portion of the femur to size the femur and select the cutting block size.

18. The method of claim 17, wherein the cutting block includes mounting holes separated by a distance equal to a distance between the two drill guide holes on the drilling arm.

* * * * *